(12) United States Patent
Maier et al.

(10) Patent No.: US 10,473,288 B2
(45) Date of Patent: Nov. 12, 2019

(54) DAYLIGHT PORTABLE LAMP FOR INSPECTING PAINTED SURFACES, IN PARTICULAR IN THE COURSE OF PAINT REPAIR WORK ON MOTOR VEHICLES

(71) Applicant: SATA GmbH & Co. KG, Kornwestheim (DE)

(72) Inventors: Norbert Maier, Allmersbach i.T. (DE); Alexander Tschan, Kornwestheim (DE)

(73) Assignee: SATA GMBH & CO. KG, Kornwestheim (DE)

( * ) Notice: Subject to any disclaimer, the term of this patent is extended or adjusted under 35 U.S.C. 154(b) by 0 days.

(21) Appl. No.: 15/678,571

(22) Filed: Aug. 16, 2017

(65) Prior Publication Data
US 2018/0051860 A1   Feb. 22, 2018

(30) Foreign Application Priority Data

Aug. 19, 2016   (DE) .......................... 20 2016 005 026

(51) Int. Cl.
| | |
|---|---|
| *F21V 1/22* | (2006.01) |
| *F21L 4/00* | (2006.01) |
| *G01N 21/88* | (2006.01) |
| *G01J 3/10* | (2006.01) |
| *G01J 3/46* | (2006.01) |
| *G01N 21/57* | (2006.01) |

(52) U.S. Cl.
CPC ................ *F21V 1/22* (2013.01); *F21L 4/005* (2013.01); *G01J 3/10* (2013.01); *G01J 3/46* (2013.01); *G01N 21/8803* (2013.01); *G01N 21/8806* (2013.01); *G01N 21/57* (2013.01); *G01N 2201/0221* (2013.01)

(58) Field of Classification Search
CPC ..................................... F21L 2/00; F21L 4/00
USPC ......................................................... 362/157
See application file for complete search history.

(56) References Cited

U.S. PATENT DOCUMENTS

| | | | |
|---|---|---|---|
| 4,963,798 A | 10/1990 | McDermott | |
| 5,418,419 A | 5/1995 | McGuire | |
| 5,746,495 A | 5/1998 | Klamm | |
| 7,679,281 B2 | 3/2010 | Kim et al. | |

(Continued)

FOREIGN PATENT DOCUMENTS

| | | |
|---|---|---|
| CA | 2299544 A1 | 9/2000 |
| CA | 2527717 A1 | 12/2004 |

(Continued)

OTHER PUBLICATIONS

German Search Report dated May 19, 2017 for Application No. 10 2016 009 956.9.

(Continued)

*Primary Examiner* — Edwyn Labaze
(74) *Attorney, Agent, or Firm* — Paul D. Bianco; Stephen Bongini; Fleit Gibbons Gutman Bongini & Bianco PL

(57) ABSTRACT

A daylight portable lamp for inspecting painted surfaces, in particular in the course of paint repair work on motor vehicles, includes at least a head part with a light-exit opening, through which the light that can be produced by the daylight portable lamp can leave, and a sleeve, which surrounds the light-exit opening and is produced from an elastic, preferably rubber-elastic, material, arranged at the light-exit opening.

16 Claims, 3 Drawing Sheets

(56) References Cited

U.S. PATENT DOCUMENTS

| | | | |
|---|---|---|---|
| 7,692,136 B2 | 4/2010 | Blees et al. | |
| 8,376,574 B2 | 2/2013 | Spartano et al. | |
| 2007/0247844 A1 | 10/2007 | Brass et al. | |
| 2008/0212319 A1* | 9/2008 | Klipstein | F21L 4/08 362/231 |
| 2014/0313706 A1* | 10/2014 | Itoh | F21V 21/30 362/184 |
| 2018/0050227 A1 | 2/2018 | Brose | |
| 2018/0054866 A1 | 2/2018 | Kruse | |

FOREIGN PATENT DOCUMENTS

| | | |
|---|---|---|
| CN | 101080594 A | 11/2007 |
| CN | 201170503 Y | 12/2008 |
| DE | 1034267 B | 7/1958 |
| DE | 1708014 A1 | 4/1971 |
| DE | 2502230 A1 | 10/1975 |
| DE | 10 2004 043 295 A1 | 3/2006 |
| DE | 20 2012 104 684 U1 | 2/2013 |
| DE | 202015005881 U1 | 11/2015 |
| DE | 10 2014 018 940 A1 | 6/2016 |
| DE | 102014018940 A1 | 6/2016 |
| GB | 1427138 A1 | 3/1976 |
| WO | 2006065589 A1 | 6/2006 |
| WO | 2016041994 A1 | 3/2016 |
| WO | 2016096387 A1 | 6/2016 |

OTHER PUBLICATIONS

German Search Report dated May 2, 2017 for Application No. 20 2016 005 026.6.
German Search Report dated May 2, 2017 for Application No. 20 2016 005 025.8.

* cited by examiner

DAYLIGHT PORTABLE LAMP FOR INSPECTING PAINTED SURFACES, IN PARTICULAR IN THE COURSE OF PAINT REPAIR WORK ON MOTOR VEHICLES

FIELD OF THE DISCLOSURE

The disclosure relates to a daylight portable lamp for inspecting painted surfaces, in particular in the course of paint repair work on motor vehicles, the daylight portable lamp having at least a head part with a light-exit opening, through which the light that can be produced by the daylight portable lamp can leave.

BACKGROUND

In various painting work, a visual inspection of painted surfaces is required. This applies in particular to the respraying of motor vehicles. Thus, a visual matching of the color of the newly painted regions with original surface regions is necessary because, in spite of the paint industry providing detailed mixing specifications for color paints, differences in color can occur in practice. Furthermore, a visual check of already painted surfaces against color shade charts, color shade panels or comparison panels is often carried out before the painting operation to determine the correct shade of color for the new painting.

Apart from checking shades of color, however, a visual inspection also serves the purpose of ascertaining further properties or defects of a painted surface. By way of example, undesired cloudiness, craters, pinholes, orange peel, fisheyes, sparkling or metallic effects or variations in the coating thickness, etc. may be mentioned.

In the case of paint repair work on motor vehicles, it must also be remembered that the painted vehicle will later be assessed and/or accepted by the customer outside in natural light. It is therefore required that an inspection of painted surfaces on motor vehicles is performed by the painter outside in natural daylight. Since, however, for reasons of environmental protection and for screening off the painting operation, the painting work, in particular on motor vehicles, is performed in enclosed areas (painting booths), there is the need for an at least preliminary inspection of the painted surface directly in the working area of the paintshop or workshop. An inspection in enclosed areas under artificial light also has the advantage that it can be performed under constant, reproducible (light) conditions. By contrast, the light conditions outside vary as a result of various influencing factors (weather, daylight, time of year, etc.).

This is the reason for the development of daylight portable lamps, which can produce a light with a relatively high light intensity that is as similar as possible to daylight, so that an authoritative assessment of painted surfaces can be carried out. After completion of the painting operation, the painter can illuminate the painted surface with the portable lamp, inspect the result of his work and, if appropriate, carry out touch-ups or corrections.

DE 10 2014 018 940 A1 discloses such a daylight portable lamp for inspecting painted surfaces in the field of motor vehicle repairs that is distinguished by a light spectrum similar to daylight along with a high light intensity.

SUMMARY

Disclosed is a daylight portable lamp for examining painted surfaces with which the adverse effects of incorrect handling are reduced.

The daylight portable lamp according to the disclosure for examining painted surfaces, in particular in the field of paint repair work on motor vehicles, has at least a head part with a light-exit opening, through which the light that can be produced by the daylight portable lamp can leave.

The daylight portable lamp according to the disclosure is distinguished by a sleeve of elastic material, which surrounds the light-exit opening. The material is preferably a rubber-elastic material.

The deformability of the sleeve reduces the risk of scratches or dents being introduced into the surface during the inspection of a product by the daylight portable lamp inadvertently coming into contact with the surface. Furthermore, the portable lamp itself is also protected from damage by the damping effect of the elastic sleeve if the head part is inadvertently struck against an object or if the portable lamp is accidentally dropped. A further advantage of the elastic sleeve is that, if it is placed on a sloping surface with the light-exit opening downward, the portable lamp cannot slide off as easily because the elastic material increases the static friction, for example in comparison with a rigid plastic.

In the case of a particularly preferred exemplary embodiment, at least the head part has a rigid-plastic housing part, on the end face of which the sleeve is fastened. This embodiment is distinguished by great stability of the head part.

An exemplary embodiment of the disclosure in which the sleeve is produced from a thermoplastic elastomer has production-related advantages in particular. Thermoplastic elastomers can be extruded, injection-molded or blow-molded, and are consequently suitable for low-cost mass production processes. By contrast, on account of the strength and the chemical resistance to organic solvents, the rigid-plastic housing part is preferably produced from polyamide.

In the case of a particularly preferred exemplary embodiment, the head part comprises a lighting element for producing the light, which is arranged in the rigid-plastic housing part. In the rigid-plastic housing part, the lighting element is protected from being damaged by the head part being compressed or crushed, the damping effect of the sleeve for example increasing the protection in the case of impact in the region of the light-exit opening.

The sleeve is preferably fastened in an interlocking and/or frictionally engaging manner, in particular on the end face of the rigid-plastic housing part. Specifically, thanks to the interlocking and/or frictionally engaging fastening, the sleeve is fastened in a captive, but detachable manner.

In the case of a particularly preferred exemplary embodiment, the fastening of the sleeve is performed by means of at least one retaining lug, which protrudes radially inwardly on the inner circumference of the sleeve. The functional reliability of this exemplary embodiment is increased by a number of retaining lugs being provided, preferably arranged such that they are uniformly distributed on the inner circumference. Provided for example on the housing part on the head side is a corresponding clearance or are a number of corresponding clearances, in which the retaining lug or the retaining lugs engage(s) when the sleeve is fitted.

The sleeve preferably performs a dual function, by the sleeve additionally serving the purpose of fastening a cover plate for the light-exit opening on the head part. The cover plate serves for protecting the internals of the head part together with the lighting element from damage and contamination. It is of particular advantage in this respect if the cover plate is exchangeable together with the detachably fastened sleeve. During the painting process the cover plate in particular may be contaminated by paints or inadvertently scratched, and so its exchangeability is of great practical advantage.

Apart from the protective function for the internals of the head part, the cover plate may preferably also have optical effects. For example, the cover plate may serve as an active optical element and for example have a color-filtering function and/or a beam-shaping effect (lens, diaphragm). The exchangeability of the cover plate may in this case also serve the purpose of varying these optical effects, in that cover plates with different optical effects are used.

In the case of a further variant of the disclosure, an optical element, such as a color filter, may also be exchangeably fastened by means of the sleeve in addition to the cover plate. Depending on the application, an optical element with the optimum properties can then be fitted. One and the same surface may also be investigated with the optical element being changed, in order to carry out inspections under different light conditions. The optical element may be freely chosen by the operator. There may however also be an electronic suggestion system, which suggests an optical element according to the characteristics of the surface, the paint, etc., so that optimum results can be achieved in the surface inspection.

For the functionally reliable securement of the cover plate, in the case of a particularly preferred exemplary embodiment the sleeve has on its inner circumference a peripheral axial bearing surface for the cover plate, on which the cover plate rests in the fitted state. By means of the peripheral bearing surface, the cover plate is pressed against the end face of the head part, in particular the end face of the rigid-plastic housing part.

To avoid a component being damaged by the head part of the lamp, the elastic sleeve is particularly important in the case of a preferred exemplary embodiment in which the handle part extends along a longitudinal axis and the head part is arranged at one end of the handle part in such a way that the end face of the head part that is provided with the light-exit opening protrudes with respect to the handle part substantially perpendicularly to the longitudinal axis of the handle part. The protruding head part is particularly at risk of colliding with the surface to be inspected, damage to which is reduced by the elastic sleeve.

In the case of a particularly preferred exemplary embodiment, the end of the handle part that is remote from the head part has an extension. The extension protrudes with respect to the handle part substantially in the same direction as the end face of the head part that is provided with the light-exit opening. This design of the portable lamp provides a form of the portable lamp in which a sufficiently large gripping space is created between the handle part and a placement surface on which the portable lamp is placed with the light-exit opening downward. The sleeve serves as an elastic supporting element.

Stable point support, in particular two-point support, is obtained at the end of the handle part that is remote from the head part, by the end face of the extension there having two projections, which can serve as (further) bearing elements.

The end face of the sleeve that is directed away from the head part is preferably curved, whereby stable point, line or area support is also obtained on the sleeve.

On account of the curvature, the sleeve preferably projects downward and upward in the middle.

It is of advantage for the handling of the daylight portable lamp according to the disclosure if the daylight portable lamp is formed as a cordless lamp operated by a rechargeable battery. A painter can pass the portable lamp along the surface to be investigated unhindered by a connection cable.

In the case of a particularly preferred exemplary embodiment, the battery is detachably fastened at the end of the handle part that is remote from the head part and the battery partially forms the extension. Since part of the extension is still present even after removal of the battery, the remaining part of the portable lamp (even without the battery) can be placed with the light-exit opening downward in a stable manner.

In the case of certain applications, for example when examining highly reflective surfaces, it is of advantage if the light intensity of the lighting element can be reduced. For this reason, in the case of a particularly preferred exemplary embodiment the light intensity of the daylight portable lamp can be set, at least can be dimmed in the range of 50-100% light intensity.

Further refinements of the disclosure are described below and shown in the accompanying figures.

BRIEF DESCRIPTION OF THE DRAWINGS

The disclosure is also explained in more detail on the basis of exemplary embodiments with reference to the accompanying figures, in which specifically.

DETAILED DESCRIPTION

Figure 1:
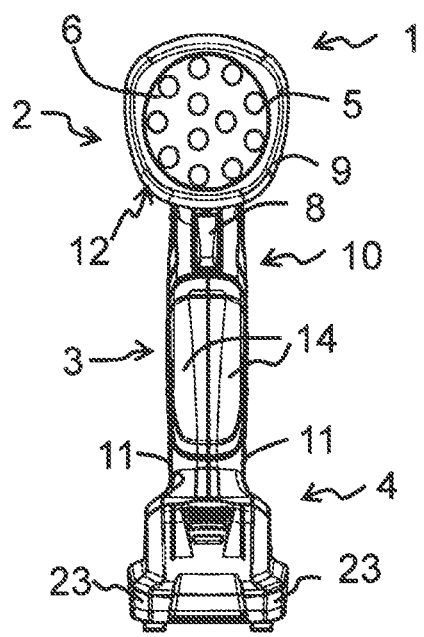
FIG. 1 shows a front view of a daylight portable lamp.
Figure 2:
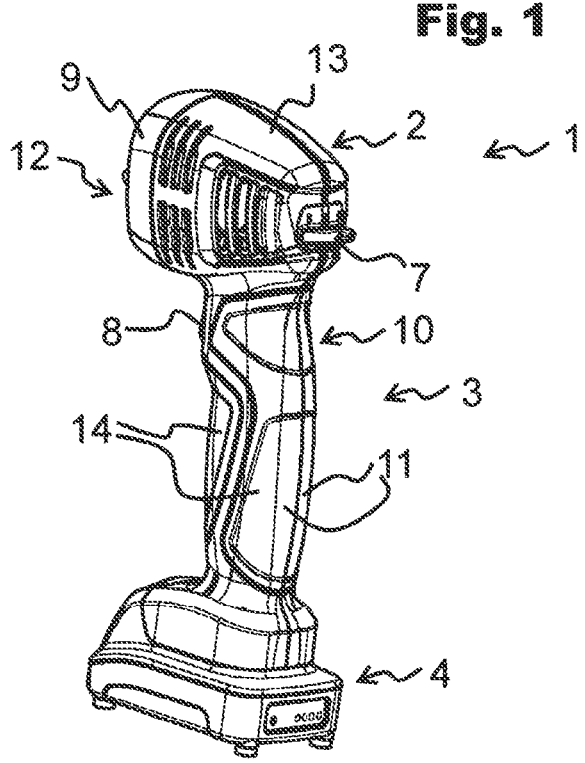
FIG. 2 shows a perspective rear view of the daylight portable lamp.

In FIGS. 1 and 2, a daylight portable lamp 1 for inspecting painted surfaces, in particular paint repair work on motor vehicles, is shown. The portable lamp 1 has a head part 2, a handle part 3 and, at the lower end of the handle part 3, a detachably fastened rechargeable battery 4, in particular an Li-ion battery. The head part 2 has on its front side a light-exit opening 5, through which a light beam can leave. For producing the light beam, a lighting element 6 is arranged in the head part 2.

Arranged on the rear side of the head part 2 is an operating element 7, by means of which the light intensity of the light beam produced can be set for example in a range from 50 to 100% of the maximum light intensity. On the side facing away from the operating element 7 and below the head part 2, a toggle switch 8 for switching the portable lamp 1 on and off is arranged.

Fastened at the light-exit opening 5 is a sleeve 9, which surrounds the light-exit opening 5 and is produced from an elastic, in particular rubber-elastic material. The rest of the housing 10 of the portable lamp 1 is produced from a rigid plastic, specifically from at least two rigid-plastic shells 11, which are put together to form the rigid-plastic housing 10.

The sleeve 9 is fastened on an end face 12 of the part 13 of the rigid-plastic housing 10 that is on the head side. For the purpose of a comfortable gripping feel and nonslip gripping of the portable lamp 1, the rigid-plastic housing 10 is partially provided with gripping surfaces 14, for example of rubber-elastic material, in the region of the handle part 3.

For example, the sleeve 9 is produced from a thermoplastic elastomer and the rigid-plastic housing 10 is produced from polyamide. It goes without saying that other elastomers can also be used for the sleeve 9 and other rigid plastics can also be used for the housing 10.

The rubber-elastic sleeve 9 reduces the risk of scratches being inadvertently introduced into a surface by the head part 2. Moreover, impact on the end face 12 of the head part 2 is damped by the sleeve 9.

Figure 3:
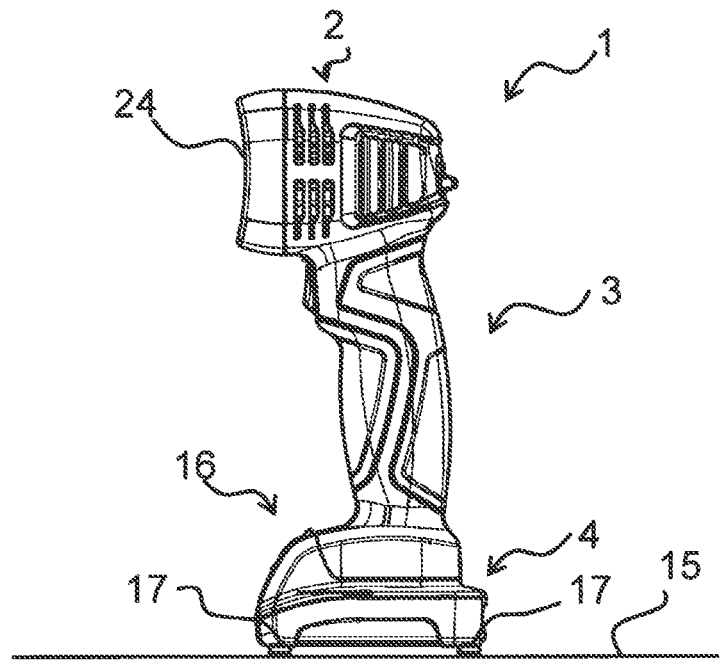
FIG. 3 shows a side view of the daylight portable lamp standing on a placement surface.
Figure 4:
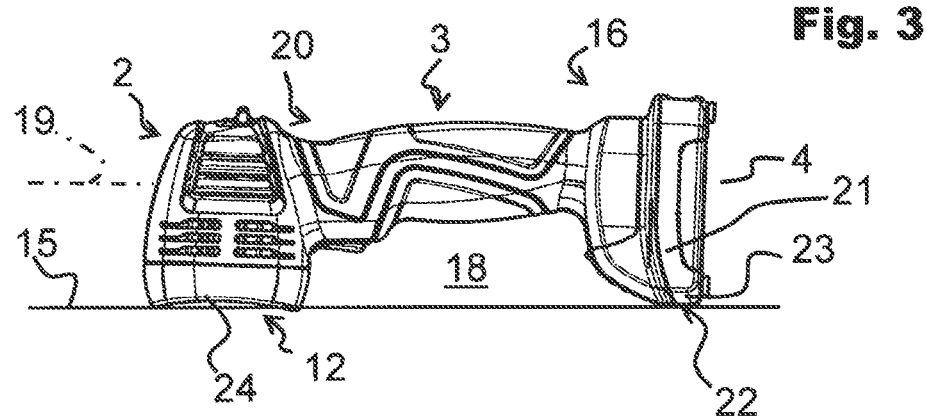
FIG. 4 shows a side view of the daylight portable lamp lying on a placement surface.
Figure 5:
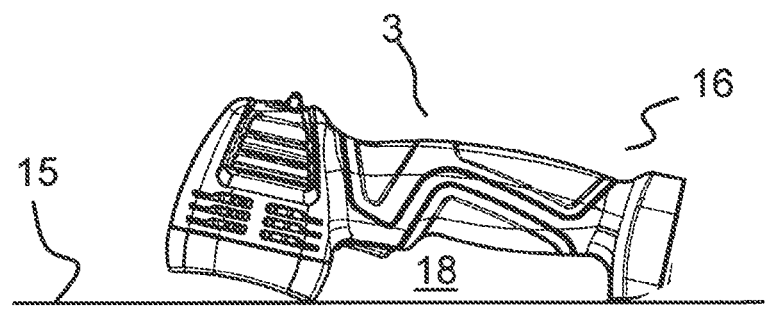
FIG. 5 shows a side view of the daylight portable lamp lying on a placement surface after removal of the battery.

A further advantage of the sleeve 9 is explained on the basis of FIGS. 3 to 5.

FIG. 3 shows a side view of the portable lamp 1, which is standing on a placement surface 15. In order to achieve stable standing, the portable lamp 1 has four standing feet 17 at the lower end 16 (remote from the head part) of the handle part 3. The standing feet 17 are part of the battery 4.

In FIG. 4, the portable lamp 1 is shown when it has been placed on the placement surface 15 with the light-exit opening 5 downward. Thanks to the increased static friction as a result of the elastic sleeve 9, the portable lamp 1 cannot slip as easily.

Furthermore, it can be seen from FIG. 4 that a sufficiently large gripping space 18 is formed between the handle part 3 and the placement surface 15, and so the lying portable lamp 1 can be easily grasped by an operator. This is a result of the overall form of the portable lamp 1, which corresponds approximately to an elongate U.

Specifically, the u shape is produced by the handle part 3 extending along a longitudinal axis 19 (FIG. 4). The head part 2 is arranged at an end 20 of the elongate handle part 3 on the head side in such a way that the end face 12 of the head part 2 protrudes with respect to the handle part 3 substantially perpendicularly to the longitudinal axis 19 of the handle part 3. Furthermore, the end 16 of the handle part 3 that is remote from the head part has an extension 21, which protrudes with respect to the handle part 3 substantially in the same direction as the head part 2 and by a similar distance.

In order that the portable lamp 1 is also stable in the lying position, the end face 22 of the extension 21 is provided with two projections 23 (FIG. 1), which can serve as bearing elements. In particular, the projections 23 are formed on the end face 22 of the battery 4. The stability is also increased by a curved design of the end face 24 of the sleeve 9. The curvature can be seen better in FIG. 6.

It is clear from FIG. 5, which shows the lying portable lamp 1 without the battery 4, that it is of advantage that the battery 4 only partially forms the extension 21. This is so because the portable lamp 1 can be placed stably even without the battery 4 on account of the remaining part of the extension 21. In addition, a sufficient gripping space 18 between the handle part 3 and the placement surface 15 also forms in this case.

It is explained below on the basis of FIGS. 6 and 7 how the rubber sleeve 9 is fastened on the end face 12 of the housing part 13. In principle, the sleeve 9 may be attached in a loose, captive, detachable or undetachable manner, etc. The sleeve 9 is preferably attached to the housing part 13 in a captive and nondestructively detachable manner.

For this purpose, the sleeve 9 is attached to the end face 12 of the rigid-plastic housing part 13 in a substantially interlocking manner. It goes without saying however that the sleeve 9 may additionally or alternatively be fastened in a frictionally engaging and/or material-bonding manner. For example, the sleeve 9 may also be additionally fixed by a thin adhesive layer.

Figure 6:
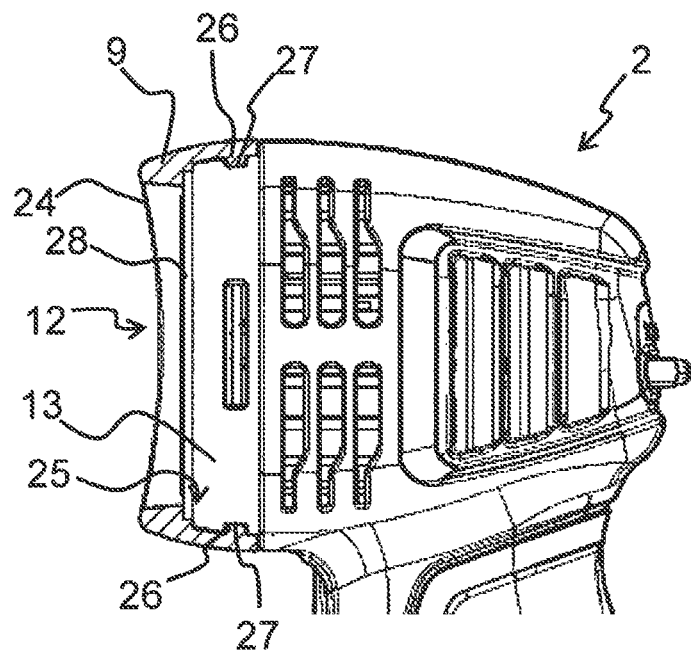
FIG. 6 shows a side view of the head part of the daylight portable lamp and FIG. 7 shows a plan view of the elastic sleeve of the head part of the daylight portable lamp.
Figure 7:
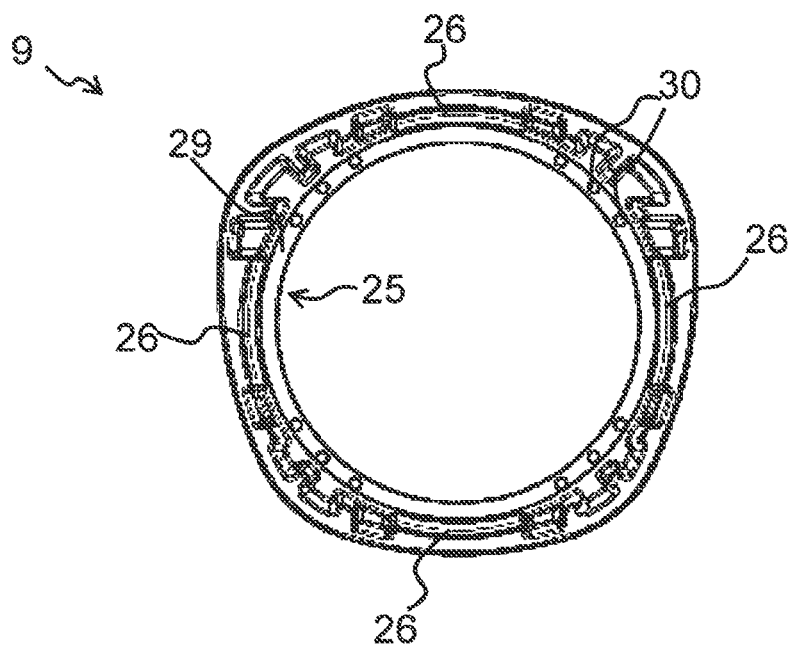

For the interlocking fastening, the sleeve 9 has on its inner circumference 25 four radially inwardly protruding retaining lugs 26 (FIG. 7), which protrude into receptacles 27 on the end face 12 of the housing part 13 (FIG. 6). On account of the deformability of the retaining lugs 26, the sleeve 9 can be fitted and removed relatively easily without having to be destroyed in the process.

A cover plate 28 for the light-exit opening 5 is fastened on the head part 2 by means of the sleeve 9. It lies loosely against the end face 12 of the housing part 13. The sleeve 9 comprises on its inner circumference 25 a peripheral axial bearing surface or shoulder 29 for the cover plate 28, on which the cover plate 28 rests in the fitted state and by means of which the cover plate 28 is pressed against the end face 12 of the rigid-plastic housing part 13. The bearing surface 29 is provided with a number of punctiform elevations 30. The cover plate 28 is exchangeable together with the sleeve 9. Alternatively, the cover plate 28 may also be clipped into the elastic material of the sleeve (groove), and then a unit can be exchanged. In the case of this variant, even after the exchange, the cover plate 28 is protected from damage by the sleeve.

In the case of a further variant that is not shown, exchangeable sleeves with different colors or identifications may be used. This allows for example a portable lamp to be assigned to an operator. The colors or identifications may also be used as an indication of the application for which the portable lamp has been set. Thus, an identification on the sleeve may for example also indicate which paints should be inspected with this portable lamp, since the lighting properties are set optimally for this inspection.

In the case of an application that is not shown, the portable lamp may also be used as a stationary illuminating means. For example, the portable lamp may be attached to a stand, a holder on the ceiling or wall of a painting booth, a tripod, a handling device (robot) or a similar fastening system. Instead of the power being supplied by means of a rechargeable battery, the portable lamp may also be connected by means of an adapter to the power grid, which adapter is for example connected to the portable lamp instead of the battery.

Generally, the portable lamp may also be connected to a control system by a cable or without a cable (for example by Bluetooth). By means of the control system, the portable lamp can for example be switched on and off or the light intensity can be set. In this case, the actuation of the on/off switch and of the setting device for the light intensity can be performed under remote control by suitable devices. The on/off switch may also remain in the set position (on or off), it being possible for the light intensity to be remotely controlled or regulated from 0% to 100%.

There may also be sensors (for example color, surface or distance sensors). On the basis of the measurement data of the sensors, the settings of the portable lamp are performed or regulated (for example light intensity distance-dependently).

A separate control system may also provide suggestions, for example for the use of color filters or other optical elements, for the light intensity, etc., with which the portable lamp should be provided or set in order to achieve optimum inspection results. This suggestion may also be effected on the basis of sensor data, for example a detection of the color, gloss, distance or surface roughness of the painted surface.

In the case of a further variant that is not shown, a head part of the portable lamp may also be arranged at an angle of 104° with respect to the longitudinal axis of a handle part. This angle has proven to be particularly ergonomic in the case of paint spray guns.

What is claimed is:

1. A daylight portable lamp for inspecting painted surfaces, in particular in the course of paint repair work on motor vehicles, the daylight portable lamp comprising:
    a head part with a light-exit opening, through which light produced by the daylight portable lamp can leave;
    an elastic sleeve arranged at the light-exit opening, the elastic sleeve surrounding the light-exit opening and produced from an elastic material; and
    a handle part extending along a longitudinal axis,
    wherein the head part is arranged at one end of the handle part in such a way that the end face of the head part that is provided with the light-exit opening protrudes with respect to the handle part substantially perpendicularly to the longitudinal axis of the handle part.

2. The daylight portable lamp of claim 1, wherein the head part has a rigid-plastic housing part, on the end face of which the sleeve is fastened.

3. The daylight portable lamp of claim 2, wherein the sleeve is produced from a thermoplastic elastomer and the rigid-plastic housing part is produced from polyamide.

4. The daylight portable lamp of claim 2, wherein the head part comprises a lighting element for producing the light, which is arranged in the rigid-plastic housing part.

5. The daylight portable lamp of claim 2, wherein the sleeve is fastened in an interlocking and/or frictionally engaging manner, in particular on the end face of the rigid-plastic housing part of the head part.

6. The daylight portable lamp of claim 2, wherein the sleeve has at least one radially inwardly protruding retaining lug, by which the sleeve is fastened, in particular on the end face of the rigid-plastic housing part of the head part.

7. The daylight portable lamp of claim 2, wherein a cover plate, which is fastened on the head part by the sleeve and is exchangeable together with the sleeve, is provided for the light-exit opening.

8. The daylight portable lamp of claim 7, wherein the sleeve has on an inner circumference a peripheral axial bearing surface for the cover plate, by which the cover plate is pressed against the end face of the head part, in particular the end face of the rigid-plastic housing part.

9. The daylight portable lamp of claim 2, wherein the elastic sleeve is fastened to the housing part in a nondestructively detachable manner.

10. The daylight portable lamp of claim 2, wherein the elastic sleeve is capable of producing an impact damping effect such that an impact in a region of the light-exit opening is damped by the elastic sleeve.

11. The daylight portable lamp of claim 2, further comprising:
    a cover plate for the light-exit opening, the elastic sleeve fastening the cover plate on the housing part,
    wherein a peripheral axial bearing surface on an inner circumference of the elastic sleeve presses the cover plate against the end face of the rigid-plastic housing part.

12. The daylight portable lamp of claim 1, wherein the end of the handle part that is remote from the head part has an extension, which protrudes with respect to the handle part substantially in the same direction as the end face of the head part that is provided with the light-exit opening.

13. The daylight portable lamp of claim 12, wherein the daylight portable lamp has a rechargeable battery, which is detachably fastened at the end of the handle part that is remote from the head part and the battery partially forms the extension.

14. The daylight portable lamp of claim 1, wherein the end face of the extension has two projections, which can serve as bearing elements.

15. The daylight portable lamp of claim 1, wherein the end face of the sleeve that is directed away from the head part is curved.

16. The daylight portable lamp of claim 1, wherein the elastic sleeve is produced from a rubber-elastic material.

* * * * *